United States Patent
Krauss et al.

(10) Patent No.: US 7,217,725 B2
(45) Date of Patent: *May 15, 2007

(54) PROSTAGLANDIN D2 ANTAGONIST

(75) Inventors: Achim H. Krauss, Foothill Ranch, CA (US); David Woodward, Lake Forest, CA (US); Yariv Donde, Dana Port, CA (US); Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 148 days.

This patent is subject to a terminal disclaimer.

(21) Appl. No.: 10/780,441

(22) Filed: Feb. 12, 2004

(65) Prior Publication Data

US 2004/0162323 A1 Aug. 19, 2004

Related U.S. Application Data

(63) Continuation-in-part of application No. 10/300,492, filed on Nov. 19, 2002, now Pat. No. 6,716,864, which is a continuation of application No. 10/071,449, filed on Feb. 8, 2002, now Pat. No. 6,511,999, which is a continuation-in-part of application No. 09/840,675, filed on Apr. 23, 2001, now Pat. No. 6,369,089, which is a continuation of application No. 09/677,372, filed on Sep. 14, 2000, now abandoned.

(51) Int. Cl.
  *A61K 31/421* (2006.01)
  *C07D 263/32* (2006.01)
(52) U.S. Cl. ...................... 514/374; 548/236
(58) Field of Classification Search ............... 548/236; 514/374
See application file for complete search history.

(56) References Cited

U.S. PATENT DOCUMENTS

| | | | |
|---|---|---|---|
| 4,808,608 A | 2/1989 | Guindon et al. | |
| 5,491,254 A | 2/1996 | Sato et al. | |
| 6,369,082 B1 | 4/2002 | Lacombe et al. | |
| 6,369,089 B1 | 4/2002 | Burk et al. | |
| 6,407,250 B1 | 6/2002 | Burk et al. | |
| 6,410,583 B1 | 6/2002 | Labelle et al. | |
| 2001/0051624 A1 | 12/2001 | Jones | |
| 2003/0055077 A1 | 3/2003 | Jones | |
| 2003/0158246 A1 | 8/2003 | Berthelette, et al. | |

FOREIGN PATENT DOCUMENTS

| | | |
|---|---|---|
| EP | 837 0582 A1 | 4/1998 |
| WO | WO 98/25919 | 6/1998 |
| WO | WO 99/62555 | 9/1999 |

OTHER PUBLICATIONS

Golub et al., Science, vol. 286, Oct. 15, 1999, pp. 531-537.*

Boie, Y, et al., "Molecular cloning and characterization of the human prostanoid DP receptor" *Journal of Biological Chemistry*, vol. 270, No. 32, Aug. 11, 1995, pp. 18910-18916.

Breyer, M.D., et al., "Functional and molecular aspects of renal prostaglandin receptors" *J. Am. Soc.Nephrol*, 1996;7:8-17.

Coleman, R.A., "Prostanoid Receptors" *Eicosanoids From Biotechnology to Therapeutic Applications*, Plenum Press, 1996, Chp. 14, 137-154.

Darius, H., et al., Inhibition of human platelets and polymorphonuclear neutrophils by the otent and metabolically stable prostaglandin D2 analog ZK 118.182 *European Journal of Pharm*, 258(1994) 207-213.

Giles, H., et al., The classification of prostaglandin DP-receptors in platelets and vasculature using BW A868C, a novel selective and potent competitive antagonist, *Br. J. Pharmacol.*, (1989), 96, 291-300.

Hirai, H, et al., "Prostaglandin D2 selectively induces chemotaxis in T helper type 2 cells, eosinophils, and basophils via seven-transmembrane receptor CRTH2", *J. Exp. Med, The Rockfeller Univ. Press*, vol. 192, No. 2, Jan. 15, 2001, 255-261.

Ichikawa, A., "Molecular aspects of the structures and functions of the prostaglandin E receptors", *J of Lipid Mediators and Cell Signalling*, 14 (1996) 83-87.

Matsuoka, T., et al., "Prostaglandin D2 as a Mediator of allergic asthma", *Science* vol. 287, Mar. 17, 2000, pp. 2013-2017.

(Continued)

*Primary Examiner*—Laura L. Stockton
(74) *Attorney, Agent, or Firm*—Brent A. Johnson; Martin A. Voet

(57) ABSTRACT

Disclosed herein is compound 1

Compound 1

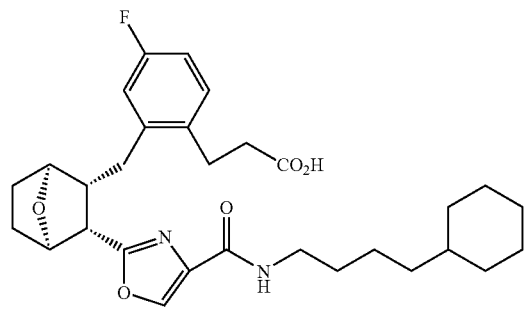

or a pharmaceutically acceptable salt, or a prodrug thereof. Compound 1 is useful for treating or preventing a variety of diseases or conditions. Results presented herein also demonstrate that Compound 1 is a prostaglandin $D_2$ antagonist, and as such is useful in the treatment or prevention of prostaglandin $D_2$ mediated conditions or diseases.

A method comprising administering a prostaglandin $D_2$ antagonist to a mammal suffering from a disease or condition selected from the group consisting of the gastrointestinal tract disorders or diseases, hyperalgesia, allodynia, abdominal cramping, glaucoma, ocular hypertension, and ocular hypotension is also disclosed herein.

Pharmaceutical compositions and products comprising compound 1 are also disclosed.

3 Claims, 4 Drawing Sheets

OTHER PUBLICATIONS

Negishi, M. et al., "Prostanoid receptors and their biological actions" *Prog. Lipid Res.* vol. 32, No. 4, pp. 417-434,1993.

Ney, P., et al., GD 2 and its mimetic ZK 110.841 are potent inhibitors of receptor-medicated activation of human neutrophils, *Eicosanoids*, 1991 4:21-28.

Pons, F., et al., "Pro-inflammatory and anti-inflammatory effects of the stable prostaglandin D2 analogue ZK. 182" *European Journal of Pharm*, 261 (1994) 237-247.

Rangachari, P.K., et al., "Effects of a selective DP receptor agonist (BW 245C) and antagonists (BW A868C) on the canine colonic epithelium : an argument for a different DP receptor", *The Journal of Pharmacology and experimental therapeutics*, vol. 275, No. 2, 611-617 (1995).

Tsuri, T., et al, "Bicyclo [2.2.1]heptane and 6,6-dimethylbicyclo[3.1.1]heptane Derivatives: orally active, potent and selective prostaglandin D2 receptor antagonists" *J. Med. Chem*, 1997, 40, 3504-3507.

Wright, D.H., et al., "A novel biological role for prostaglandin D2 is suggested by distribution studies of the rat DP prostanoid receptor", *European Journal of Pharmacology*, 377 (1999) 101-115.

Wright, D.H., et al., "Characterization of the recombinant human prostanoid DP receptor and identification of L-644,698, a novel selective DP agonist", *British J. of Pharm.* (*1998*) *123,1317-1324.*

\* cited by examiner (a) CH₃I, DBU, acetone; (b) DIBAL, toluene -78 °C to rt; (c) PDC, MgSO₄, 4Å molecular sieves, CH₂Cl₂ 74% from 1; (d) Ph₃PCHCO₂CH₃, toluene 95%;
(e) (Ph₃P)₃RhCl, H₂, EtOH 80%; (f) DIBAL, toluene -78 °C to rt 99%;
(g) Dimethylthexylsilyl chloride, DMAP, Et₃N, CH₂Cl₂ 83%.

(a) Mg, THF, 65 °C; (b) EtMgBr, 0 °C to rt 69%; (c) Ac$_2$O, pyridine 77%; (d) (Im)$_2$S, ClCH$_2$CH$_2$Cl, 60 °C 94%; (e) n-Bu$_3$SnH, AIBN, toluene, 110 °C 84%; (f) CrO$_3$, H$_2$SO$_4$, acetone; (g) MeOH, AcCl 88% for 2 steps; (h) CrO$_3$, H$_2$SO$_4$, acetone.

(a) L-serine benzyl ester hydrochloride, DCC, HOBt, Et$_3$N, THF 80% for 2 steps;
(b) PPh$_3$, CCl$_4$, i-Pr$_2$NEt, CH$_3$CN 69%; (c) BrCCl$_3$, DBU, CH$_2$Cl$_2$ 0 °C 75%; (d) H$_2$, Pd(OH)$_2$/C, EtOAc 100%; (e) i. (COCl)$_2$, cat. DMF, CH$_2$Cl$_2$; ii. 4-cyclohexylbutylammonium chloride, Et$_3$N, CH$_2$Cl$_2$ 78%; (f) NaOH, aqueous THF, 95%.

PROSTAGLANDIN D2 ANTAGONIST

CROSS-REFERENCE TO RELATED APPLICATIONS

This application is a continuation-in-part of U.S. patent application Ser. No. 10/300,492, filed on Nov. 19, 2002; now U.S. Pat. No. 6,716,864 which is a continuation of U.S. patent application Ser. No. 10/071,449, now U.S. Pat. No. 6,511,999, filed on Feb. 8, 2002; which is a continuation-in-part of U.S. patent application Ser. No. 09/840,675, now U.S. Pat. No. 6,369,089 filed on Apr. 23, 2001; which is a continuation of U.S. patent application Ser. No. 09/677,372 filed Sep. 14, 2000, now abandoned. All of the aforementioned patent applications are incorporated by reference herein.

Said U.S. Pat. No. 6,369,089 filed on Apr. 23, 2001; which is a continuation of U.S. patent application Ser. No. 09/677,372 filed Sep. 14, 2000, now abandoned, is also related to U.S. application Ser. No. 09/661,771, also filed Sep. 14, 2000, now U.S. Pat. No. 6,407,250 which was incorporated by reference therein.

Thus, the present application claims priority to the disclosure of all of the foregoing patent applications, and the effective filing dates of the material in any of said applications is identical to the effective filing date of said material in the present application.

BACKGROUND OF THE INVENTION

1. Field of the Invention

This disclosure relates to pharmaceutical compositions and medical treatments. In particular, this disclosure relates to the use of prostaglandin $D_2$ antagonists in said compositions and treatments.

2. Description of the Related Art

The potential of prostaglandin $D_2$ antagonists in the treatment of allergy-related conditions is well documented and supported in the open literature, for example, Matsuoka and colleagues reported that "$PGD_2$ functions as a mediator of allergic asthma . . . it may also play an important role in other allergic disorders such as allergic rhinitis and atopic dermatitis. The DP receptor may thus represent a new therapeutic target for the treatment of such allergic reactions." (Science, vol 298, 17 Mar. 2000) Similar disclosures are found in Tsuri (J. Med. Chem., 40 (22), 3504–3507, 1997), Hirai (J. Exp. Med., 193, Number 2, Jan. 15, 2001 255–261), and several patent documents, including U.S. patent publication 20030055077 and U.S. Pat. No. 6,083,974, which teach the use of prostaglandin D2 antagonists for the treatment of certain allergic conditions.

The relationship between prostaglandin D2 and systemic mastocytosis is also known. Negishi teaches "Systemic mastocytosis is a disease in which the mast cell population increases in various tissues and produces $PGD_2$. Prominent symptoms are vasodilation manifested by flushing, tachycardia and occasionally hypotension and clyspnea, and increased intestinal motility resulting in abdominal cramping, diarrhea, nausea and vomiting." (Prog. Lip. Res., vol 32, no. 4, pp 417–434, 1993)

U.S. Pat. No. 6,083,974 teaches the use of $PGD_2$ antagonists "as drugs for treating diseases in which mast cell dysfunction is involved, for example, systemic mastocytosis and disorder of systemic mast cell activation as well as for tracheal contraction, asthma, allergic rhinitis, allergic conjunctivitis, urticaria, ischemic reperfusion injury, inflammation, and atopic dermatitis."

Wright teaches that prostaglandin $D_2$ regulates mucous secretion, and has "both contractile and a relaxant role . . . in the gastrointestinal tract", and that "the DP receptor may mediate mucous secretion and cytoprotection". (European Journal of Pharmacology 377 (1999) 101–115)

In addition to the aforementioned conditions, U.S. Pat. No. 6,410,583 teaches the use of prostaglandin $D_2$ antagonists for the treatment of pulmonary congestion.

Additionally U.S. Patent Publication 20030158246 discloses prostaglandin D2 antagonists which "are useful to treat, prevent, or ameliorate in mammals and especially in humans: respiratory conditions, allergic conditions, pain, inflammatory conditions, mucus secretion disorders, bone disorders, sleep disorders, fertility disorders, blood coagulation disorders, trouble of the vision as well as immune and autoimmune diseases. In addition, such a compound may inhibit cellular neoplastic transformations and metastic tumor growth and hence can be used in the treatment of cancer." Additionally, the '246 publication discloses that the prostaglandin $D_2$ antagonists "may also be of use in the treatment and/or prevention of prostaglandin $D_2$ mediated proliferation disorders such as may occur in diabetic retinopathy and tumor angiogenesis." The '246 publication also teaches the use of prostaglandin $D_2$ antagonists for the treatment and/or prevention of "allergic rhinitis, nasal congestion, rhinorrhea, perennial rhinitis, nasal inflammation, asthma including allergic asthma, chronic obstructive pulmonary diseases and other forms of lung inflammation; pulmonary hypotension; sleep disorders and sleep-wake cycle disorders; prostanoid-induced smooth muscle contraction associated with dysmenorrhea and premature labor; eosinophil-related disorders; thrombosis; glaucoma and vision disorders; occlusive vascular diseases, such as for example atherosclerosis; congestive heart failure; diseases or conditions requiring a treatment of anti-coagulation such as post-injury or post surgery treatment; rheumatoid arthritis and other inflammatory diseases; gangrene; Raynaud's disease; mucus secretion disorders including cytoprotection; pain and migraine; diseases requiring control of bone formation and resorption such as for example osteoporosis; shock; thermal regulation including fever; rejection in organ transplant and by-pass surgery, and immune disorders or conditions in which immunoregulation is desirable. More particularly the disease to be treated is one mediated by prostaglandin $D_2$ such as nasal congestion, allergic rhinitis, pulmonary congestion, and asthma including allergic asthma."

In citing the foregoing references, and other references cited herein, applications make no admission as to whether any of said references constitutes prior art. Rather, the determination of what constitutes prior art is a legal decision made on the basis of the dates said references were made available to the public, the authors or inventors of said references, and the effective filing date of the disclosure made herein.

BRIEF DESCRIPTION OF THE INVENTION

Disclosed herein are methods and compositions related to compound 1

Compound 1

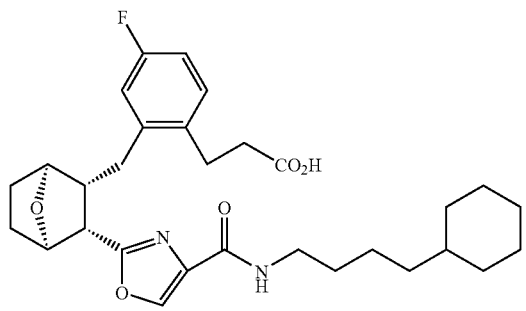

or a pharmaceutically acceptable salt, or a prodrug thereof (all of which are referred to hereafter, collectively or individually, as "compound 1"), which is an antagonist of a prostaglandin DP receptor, or is a prostaglandin $D_2$ antagonist.

Also disclosed are methods of treating or preventing a prostaglandin $D_2$ mediated condition or disease with compound 1 shown above, or a pharmaceutically acceptable salt, or a prodrug thereof.

A method comprising administering a prostaglandin $D_2$ antagonist to a mammal suffering from a disease or condition selected from the group consisting of the gastrointestinal tract disorders or diseases, hyperalgesia, allodynia, abdominal cramping, glaucoma, ocular hypertension, and ocular hypotension is also disclosed herein.

BRIEF DESCRIPTION OF THE DRAWING FIGURES

DETAILED DESCRIPTION OF THE INVENTION

Figure 1:
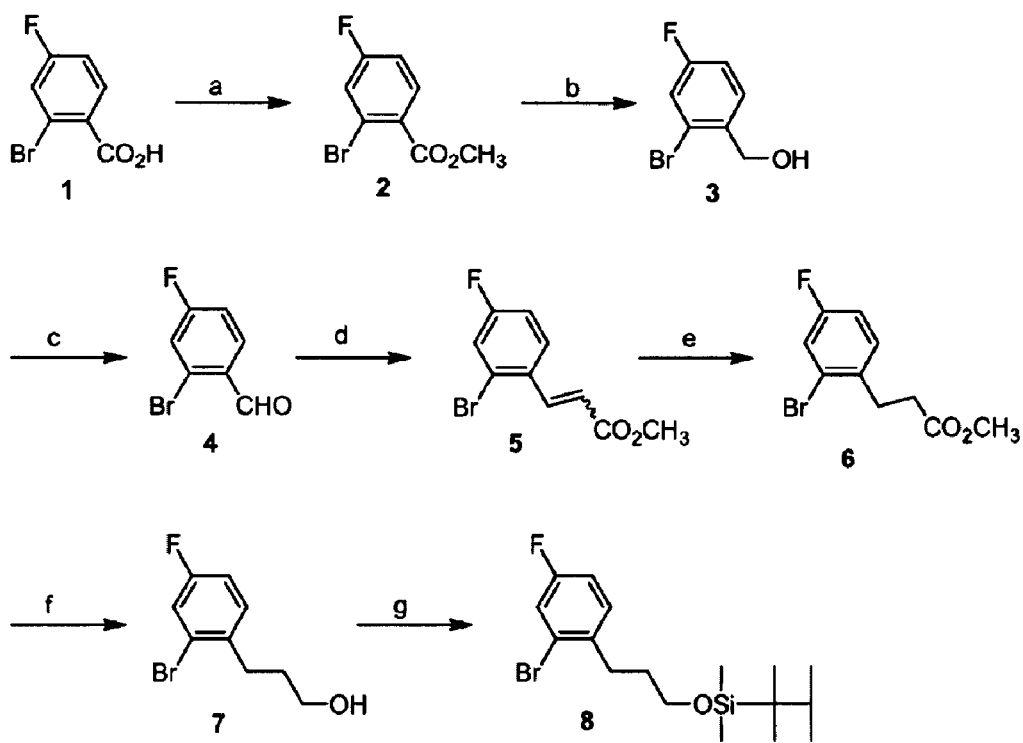
FIGS. 1–3 illustrate one synthetic method for obtaining compound 1.

One embodiment comprises compound 1. Compound 1 is used in a medical sense to treat or prevent a prostaglandin $D_2$ mediated condition or disease, or a disease which is mediated by a prostaglandin DP receptor.

A prostaglandin $D_2$ mediated condition or disease is broadly interpreted as a disease or condition wherein the amount of prostaglandin $D_2$ in an animal body or in a particular part of the body, or the flux or balance of prostaglandin $D_2$ in the body or a particular part of the body causes or contributes to the cause of a disease or condition, or a symptom thereof. A condition or disease which is mediated by the prostaglandin DP receptor is one in which the binding or lack of binding, or the agonism or antagonism of the prostaglandin DP receptor, causes or contributes to the cause of a disease or condition, or a symptom thereof.

While not intending to limit the scope of the invention in any way, one function of prostaglandin $D_2$ is immune modulation. As such, diseases related to immune function, including immune and autoimmune disease such as HIV or AIDS, can be treated by prostaglandin $D_2$ antagonist.

Other prostaglandin $D_2$ mediated conditions or diseases include inflammatory disorders such as nasal inflammation, lung inflammation including chronic obstructive pulmonary diseases, asthma, dermatitis, and edema.

Prostadglandin $D_2$ mediated conditions or diseases also include allergic diseases and the symptoms thereof, such as nasal congestion, rhinitis, and asthma. In one embodiment, the condition is a dermatological allergy. In another embodiment, the condition is an ocular allergy. In another method, the condition is a respiratory allergy.

Prostaglandin $D_2$ is also related to the modulation of pain, and as such mediates conditions or diseases related to pain, such as hyperalgesia, allodynia, headache, arthritis, and migraine. Prostaglandin $D_2$ also contributes to the modulation of mucus secretion, including gastrointestinal mucus secretion, and mucus secretion which occurs in the nose, sinuses, throat, or lungs.

Prostaglandin $D_2$ also mediates gastrointestinal mucus secretion and cytoprotection, and as such is related to conditions and diseases associated with the gastrointesintal tract, such as, peptic ulcer, heartburn, reflux esophagitis, erosive esophagitis, non-ulcer dyspepsia, infection by Helicobacter pylori, alrynitis, and irritable bowel syndrome.

Prostaglandin $D_2$ also mediates abdominal cramping. Prostaglandin $D_2$ antagonists, including compound 1, are thus useful in treating abdominal cramping and related conditions or disease.

Prostaglandin $D_2$ also mediates bleeding and blood coagulation disorders, sleep-wake cycle disorders, and sleep disorders, and mastocytosis and abnormally high systemic and local production of $PGD_2$, which causes symptoms such as flushing, tachycardia, hypotension, clyspnea, increased intestinal motility, abdominal cramping, diarrhea, nausea, and vomiting.

Other diseases or conditions mediated by prostaglandin $D_2$ or a prostaglandin DP receptor, and thus are treated by prostaglandin $D_2$ antagonists including compound 1, include allergic conditions, atherosclerosis, bone disorders, cancer, cellular neoplastic transformations, and other forms, congestive heart failure, diabetic retinopathy, diseases or conditions requiring a treatment of anti-coagulation, diseases requiring control of bone formation and resorption, elevated body temperature, fertility disorders, fever, gangrene, glaucoma, hypothermia, metastic tumor growth, migraine, mucus secretion disorders, occlusive vascular diseases, ocular hypertension, ocular hypotension, osteoporosis, perennial rhinitis, pulmonary congestion, pulmonary hypotension, Raynaud's disease, rejection in organ transplant and by-pass surgery, respiratory conditions, rheumatoid arthritis, rhinorrhea, shock, and tumor angiogenesis.

In other embodiments, a prostaglandin $D_2$ antagonist is used to prevent or treat a condition selected from the group consisting of gastrointestinal tract disorders or diseases, hyperalgesia, allodynia, abdominal cramping, glaucoma, ocular hypertension, and ocular hypotension.

In one embodiment, a prostaglandin $D_2$ antagonist is used to prevent or treat a gastrointestinal tract disorder or disease such as peptic ulcer, heartburn, reflux esophagitis, erosive esophagitis, non-ulcer dyspepsia, infection by *Helicobacter pylori*, alrynitis, and irritable bowel syndrome. In another method, a prostaglandin $D_2$ antagonist is used to prevent or treat irritable bowel syndrome. In another embodiment, a prostaglandin $D_2$ antagonist is used to prevent or treat hyperalgesia or allodynia. In another embodiment a prostaglandin $D_2$ antagonist is used to prevent or treat abdominal cramping.

In another method a prostaglandin $D_2$ antagonist is used to prevent or treat a condition or disease associated with ocular hypertension and glaucoma. In another embodiment, said a prostaglandin $D_2$ antagonist is used to prevent or treat a condition or disease associated with ocular hypotension.

Other embodiments relate to compositions comprising compound 1 or a pharmaceutically acceptable salt or a prodrug thereof and a pharmaceutically acceptable excipient.

Other embodiments relate to methods comprising treating or preventing a condition or disease selected from the group consisting of allergic conditions, asthma, allergic asthma, allergic rhinitis, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, fertility disorders, fever, gangrene, glaucoma, hypothermia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, pain, perennial rhinitis, pulmonary congestion, pulmonary hypotension, Raynaud's disease, rejection in organ transplant and by-pass surgery, respiratory conditions, rheumatoid arthritis, rhinorrhea, shock, sleep disorders, sleep-wake cycle disorders, and tumor angiogenesis. In each of these methods, compound 1 is administered to a mammal suffering from said condition or disease.

A "pharmaceutically acceptable salt" is any salt that retains the activity of the parent compound and does not impart any additional deleterious or untoward effects on the subject to which it is administered and in the context in which it is administered compared to the parent compound.

Pharmaceutically acceptable salts of acidic functional groups may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted.

Those skilled in the art will readily understand that for administration the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgement of the prescribing physician. The therapeutically effective dosage of the presently useful compound or compounds is preferably in the range of about 0.5 or about 1 to about 100 mg/kg/day.

For ophthalmic application, solutions are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edentate disodium, although other chelating agents may also be used in place or in conjunction with it.

The ingredients are usually used in the following amounts:

| Ingredient | Amount (% w/v) |
|---|---|
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

Figure 2:
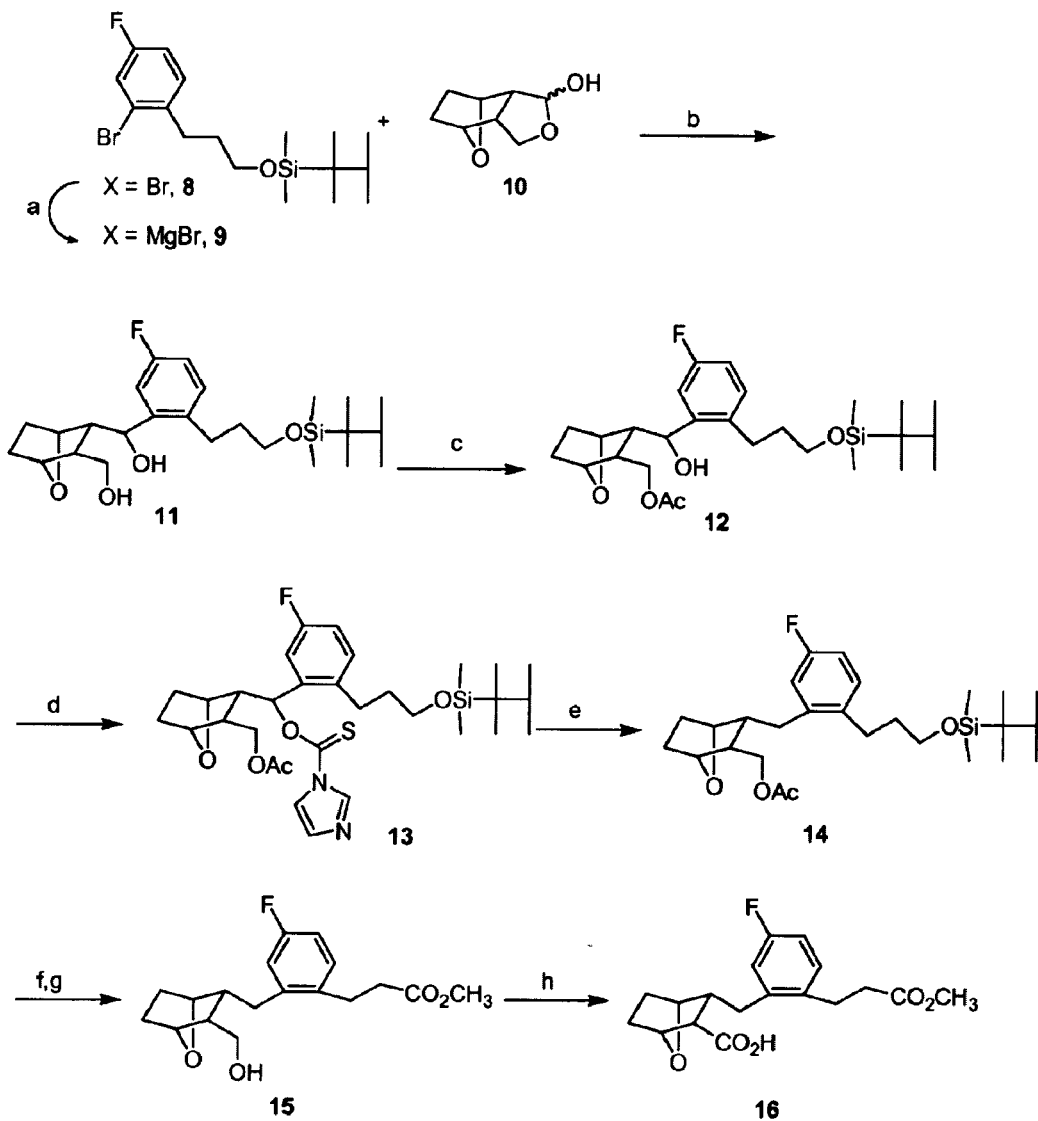
Figure 3:
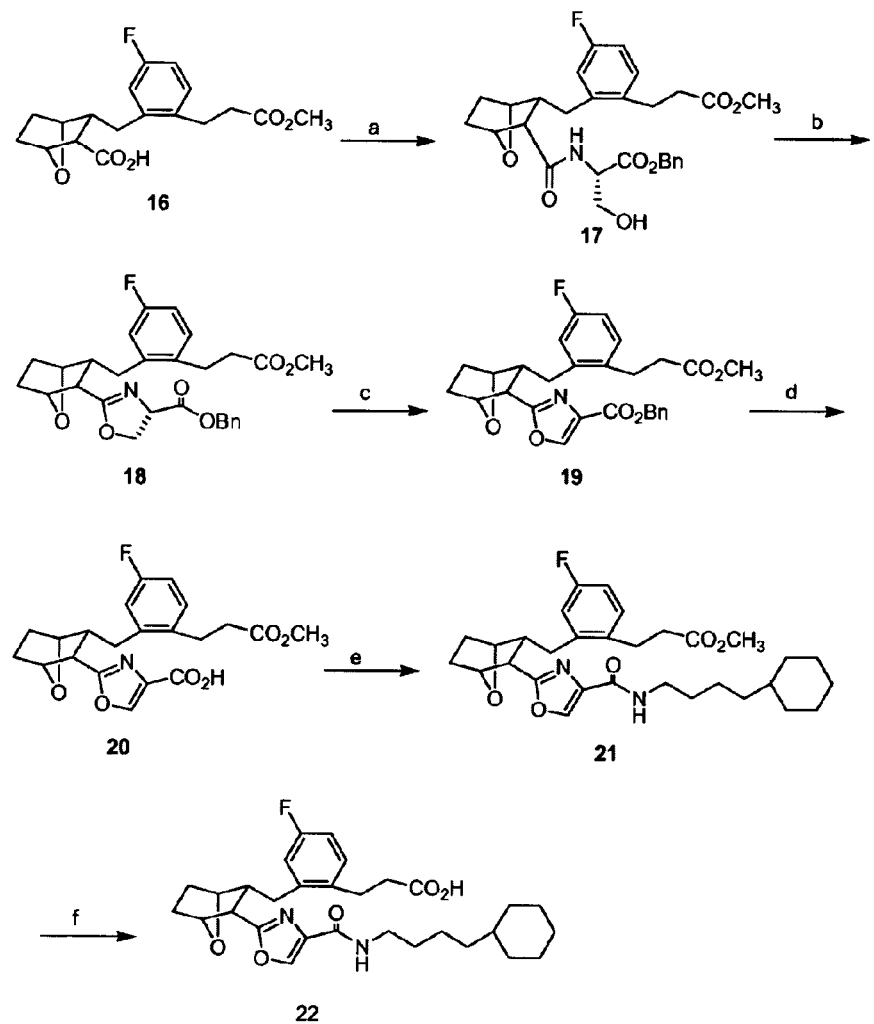

The following Examples 1–22 describe a method of synthesizing the compound shown herein to be a prostaglandin $D_2$ antagonist, wherein the numbering of the Examples corresponds to the numbering of the various intermediates and final compounds shown in FIGS. 1 through 3.

EXAMPLE 1

2-Bromo-4-fluorobenzoic acid. The named compound is purchased from Marshallton Research Laboratories Inc., P.O. Box 930, King, N.C. 27021.

EXAMPLE 2

2-Bromo-4-fluorobenzoic acid, methylester. A solution of 2-bromo-4-fluorobenzoic acid (5 g, 22.8 mmol), DBU (5.21 g, 34.2 mmol), and methyl iodide (6.48 g, 45.7 mmol) in acetone (23 mL) was stirred at room temperature for 2 h. The reaction was concentrated in vacuo and the residue partitioned between EtOAc and 1 M HCl. The organic portion was washed with saturated aqueous $NaHCO_3$, brine and then was dried ($MgSO_4$), filtered and evaporated to give the ester of Example 2 (5.18 g) which was used directly in the next step.

EXAMPLE 3

(2-Bromo-4-fluorophenyl) methanol. DIBAL-H (56 mL, 56 mmol, 1M/toluene) was added to a solution of the ester of Example 2 (5.18 g, 22.2 mmol) in toluene (50 mL) at −78° C. After 1 h, the reaction was warmed to room temperature and quenched by dropwise addition of 1 M NaOH. The mixture was extracted with EtOAc. The organic portion was washed with brine and then was dried ($MgSO_4$), filtered, and evaporated to give the alcohol of Example 3 (4.55 g) which was used directly in the next step.

EXAMPLE 4

2-Bromo-4-fluorobenzaldehyde. A mixture of the alcohol of Example 3 (4.55 g, 22.2 mmol), PDC (10.0 g, 26.6 mmol), $MgSO_4$ (10.0 g) and crushed 4 Å molecular sieves (10.0 g) in $CH_2Cl_2$ (44 mL) was stirred for 12 h. The mixture was diluted with ether and filtered through celite. The solvent was evaporated and the residue purified by flash column chromatography on silica gel (10% EtOAc/hexanes) to give the aldehyde of Example 4 (3.43 g, 16.9 mmol, 74% from 2-bromo-4-fluorobenzoic acid).

EXAMPLE 5

(E)-3-(2-Bromo-4-fluorophenyl)acrylic acid methyl ester. A mixture of the aldehyde of Example 4 (4.5 g, 22.2 mmol) and methyl(triphenylphosphoranylidene)acetate (8.91 g, 36.6 mmol) in toluene (22 mL) was stirred for 12 h. The solvent was removed in vacuo and the residue was purified by flash chromatography on silica gel (5% EtOAc/hexanes) to give the ester of Example 5 (5.46 g, 21.1 mmol, 95%).

EXAMPLE 6

3-(2-Bromo-4-fluorophenyl)propionic acid methyl ester. A mixture of $(Ph_3P)_3RhCl$ (1.49 g, 1.61 mmol) and the ester of Example 5 (4.17 g, 16.1 mmol) in ethanol (30 mL) was evacuated and purged with $H_{2(g)}$. The mixture was stirred under 1 atm $H_2$ pressure for 12 h. The solvent was removed and the residue was purified by flash column chromatography on silica gel (5% EtOAc/hexanes) to give the ester of Example 6 (3.50 g, 13.4 mmol, 80%).

EXAMPLE 7

3-(2-Bromo-4-fluorophenyl)propan-1-ol. A −78° C. solution of the ester of Example 6 (3.50 g, 13.4 mmol) in toluene (20 mL) was treated dropwise with DIBAL-H (33.5 mL, 33.5 mmol, 1 M/toluene). After 1 h, the reaction was warmed to room temperature and then was quenched with dropwise addition of 1 M $H_2SO_4$. The warm mixture was poured onto ice and extracted with EtOAc. The organic portion was washed with saturated $NaHCO_3$ solution and brine and then was dried ($MgSO_4$), filtered, and evaporated. Purification by flash column chromatography on silica gel (25% EtOAc/hexanes) gave the alcohol of Example 7 (3.09 g, 13.3 mmol, 99%).

EXAMPLE 8

[3-(2-Bromo-4-fluoro-phenyl)-propoxyl]-dimethyl-(1,1,2-trimethyl-propyl)-silane. A solution of the alcohol of Example 7, (2.1 g, 9.0 mmol), dimethylthexylsilyl chloride (2.8 mL, 14.2 mmol, Aldrich), $Et_3N$ (1.36 mL, 9.76 mmol, Aldrich) and 4-(dimethylamino)pyridine (48 mg, 0.39 mmol, Aldrich) in $CH_2Cl_2$ (16 mL, Aldrich) was stirred for 18 h. The solution was poured into saturated aqueous $NaHCO_3$ solution (25 mL) and the mixture extracted with $CH_2Cl_2$ (2×25 mL). The combined $CH_2Cl_2$ solution was dried ($MgSO_4$), filtered, evaporated and purified by flash column chromatography on silica gel (2% EtOAc/hexanes→30%→40%) to give the silane of Example 8 (2.792 g, 7.4 mmol, 83%).

EXAMPLE 9

A mixture of Mg turnings (173 mg, 7.1 mmol, Aldrich), iodine (2 crystals), and 1,2-dibromoethane (20 μL) in dry THF (2.6 mL, Aldrich) was heated in a 64° C. oil bath with magnetic stirring until the iodine color disappeared (ca. 15 min.). The resulting mixture was allowed to cool to room temperature and a solution of the bromide of Example 8 (1.882 g, 5.0 mmol) in 1.5 mL THF was added dropwise by cannula, rinsing with 1 mL THF. The mixture was heated in the 64° C. oil bath for 3 h, allowed to cool to room temperature and used directly in the next step.

EXAMPLE 10

3aR-(3aα,4α,7α,7aα)]-1-Hydroxyhexahydro-4,7-epoxy-isobenzofuran. The named compound is prepared according to Das, J.; Haslanger, M. F.; Gougougoutas, J. Z.; Malley, M. F. Synthesis of Optically Active 7-Oxabicyclo [2.2.1]heptanes and Assignment of Absolute Configuration. *Synthesis* 1987, 1100–1103 except in the final dibal reduction of the corresponding lactone, the reaction was quenced with methanol and worked up with aqueous NaOH.

EXAMPLE 11

1-(2-{3-[Dimethyl-(1,1,2-trimethyl-propyl)-silanyloxy]-propyl}-5-fluoro-phenyl)-1-((1R, 2S, 3R, 4R-3-hydroxymethyl-7-oxa-bicyclo[2.21]hept-2-yl)-methanol. An ice-cold solution of lactol 10 (3aR-(3aα,4α,7α,7aα)]-1-Hydroxyhexahydro-4,7-epoxyisobenzofuran (708 mg, 4.53 mmol) in 2.4 mL of dry THF (Aldrich) was treated dropwise with EtMgBr (4.5 mL, 4.5 mmol, 1 M/THF, Aldrich). After 20 min., the Grignard solution from Example 9 above was added by cannula and the solution allowed to warm to room temperature.

After 16 h, the reaction was quenched by addition of 2.8 mL of saturated NH$_4$Cl solution with cooling. The resulting mixture was stirred for 2 h and then CH$_2$Cl$_2$ (10 mL) was added. The solution was decanted from the gum, the gum washed further with CH$_2$Cl$_2$ (3×10 mL), and the combined CH$_2$Cl$_2$ solution was dried (MgSO$_4$), filtered, and evaporated. Purification of the crude product by flash column chromatography on silica gel (40% EtOAc/hexanes) gave the diol of Example 11 (1.386 g, 3.1 mmol, 69%) as an oil.

EXAMPLE 12

Acetic acid (1R,2R,3S,4R)-3-[1-(2-{3-[dimethyl-(1,1,2-trimethyl-propyl)-silanyl oxy[-propyl}-5-fluoro-phenyl)-1-hydroxy-methyl]-7-oxa-bicyclo[2.2.1]hept-2-ylmethl ester. The diol of Example 11 (713 mg, 1.62 mmol) was co-evaporated with benzene (2×2 mL). The residue was taken into 1.5 mL of dry pyridine (Aldrich) and was treated with Ac$_2$O (195 μL, 2.07 mmol, Aldrich). The solution was allowed to stir for 17 h and then was evaporated and co-evaporated twice with toluene. Flash column chromatography on silica gel (20% EtOAc/hexanes→30%→40%→50%) gave the monoacetate of Example 12 (564 mg, 1.17 mmol, 72%).

EXAMPLE 13

Acetic Acid (1R,2R,3R,4R)-3-[1-(2-{3-[dimethyl-(1,1,2-trimethyl-propyl)-silanyl oxy)-propyl}-5-fluoro-phenyl)-1-(1-imadazol-1-yl-methanethioyloxy)-methyl]-7-oxa-bicyclo]2.2.1]hept -2ylmethyl ester. The acetate of Example 12 (5.64 mg, 1.17 mmol) was co-evaporated with benzene (2×2 mL). The residue was taken into dry dichloroethane (0.8 mL, Aldrich) and thiocarbonyldiimidazole (643 mg, 3.61 mmol, Aldrich) was added. The mixture was heated in a 60° C. oil bath with stirring. After 1 h, there was a considerable amount of starting material and so the solvent level was reduced under a nitrogen stream and the reaction allowed to stir further for another 1 h at which time the reaction was complete (TLC analysis). The mixture was allowed to cool to room temperature and then purified by flash column chromatography on silica gel (30% EtOAc/hexanes→40%) which gave the ester of Example 13 (506 mg, 0.93 mmol, 79%).

EXAMPLE 14

Acetic acid (1R,2R,3R,4R)-3-(2-{3-[dimethyl-(1,1,2-trimethyl-propyl)-silanyloxy]-propyl}-5-fluoro-benzyl)-7-oxa-bicyclo[2.2.1]hept-2-ylmethyl ester. A solution of the ester of Example 13 (506 mg, 0.93 mmol), Bu$_3$SnH (1.44 mL, 5.35 mmol, Aldrich), and AIBN (53 mg, 0.32 mmol, Alfa) in toluene (45 mL, Aldrich) was heated in a 110° C. oil bath. After 2 h, the reaction was not complete (TLC analysis) and so another 53 mg of AIBN was added. After 1 h of further heating the reaction was complete. The solution was allowed to cool to room temperature, was evaporated and then purified by flash column chromatography on silica gel (100% hexanes→5% EtOAc/hexanes→10%) which gave the ester of Example 14 (366 mg, 0.78 mmol, 84%).

EXAMPLE 15

3-[4-Fluoro-2-((1R,2R,3R,4R)-3-hydroxymethyl-7-oxa-bicyclo[2.2.1]hept-2-ylmethyl)-phenyl]-propionic acid methyl ester. A solution of the ester of Example 14 (577 mg, 1.2 mmol) in acetone (6 mL, B & J brand) was treated dropwise with Jones reagent (0.84 mL, 2.5 M in Cr(VI), 2.1 mmol). After 20 min., the reaction was quenched by addition of isopropyl alcohol (0.5 mL). The mixture was allowed to stir for 15 min. and then was filtered through celite. The filtrate was evaporated and the residue was partitioned between CH$_2$Cl$_2$ (20 mL) and 3:1 H$_2$O/brine (20 mL). The aqueous portion was further extracted with CH$_2$Cl$_2$ (2×20 mL) and the combined CH$_2$Cl$_2$ solution was dried (MgSO$_4$), filtered and evaporated to leave the acid as a slightly yellow oil that was used directly in the next step.

The crude acid was taken into a solution of 1% v/v AcCl/MeOH (3.5 mL). After 20 h, NaHCO$_3$ (110 mg) was added and the mixture diluted with diethyl ether (20 mL). The mixture was dried (MgSO$_4$), filtered, evaporated, and purified by flash column chromatography on silica gel (60% EtOAc/hexanes→67%→75%) which gave 15 3-[4-Fluoro-2-((1R,2R,3R,4R)-3-hydroxymethyl-7oxa-bicyclo[2.2.1] hept-2-ylmethyl)-phenyl]-propionic acid methyl ester (339 mg, 1.05 mmol, 88% from the ester of Example 14).

EXAMPLE 16

(1R,2S,3R,4R)-3-[5-fluoro-2-(2-methoxycarbonyl-ethyl)-benzyl]phenyl)-7-oxa-bicyclo [2.2.1]heptane-2-carboxylic acid. A solution of the ester of Example 15 (336 mg, 1.04 mmol) in acetone (8 mL, B & J brand) was treated dropwise with Jones reagent (0.8 mL, 2.0 mmol, 2.5 M). The orange mixture was allowed to stir for 35 min. and then was quenched by addition of 0.5 mL isopropyl alcohol. After 15 min., the mixture was filtered through celite and evaporated. The residue was partitioned between 10 mL 1 M HCl and 20 mL CH$_2$Cl$_2$. The aqueous layer was extracted further with CH$_2$Cl$_2$ (2×20 mL) and the combined CH$_2$Cl$_2$ solution dried (MgSO$_4$), filtered and evaporated to give crude 16 (338 mg, 1.00 mmol, 97%).

EXAMPLE 17

(S)-2[(1-{(1R,2S,3R,4R)- 3-5-fluoro-2-(2-methoxycarbonyl-ethyl)-benzyl ]-7-oxa-bicyclo[2.2.1]hept-2-yl}-methanoyl)-amino]-3-hydroxy-propionic acid benzyl ester. The crude acid 16 (338 mg, 1.00 mmol,) was co-evaporated with benzene and the residue was taken into dry THF (4.3 mL, Aldrich). The solution was cooled in an ice bath and 1-hydroxybenzotriazole monohydrate (188 mg, 1.39 mmol, Aldrich), L-serine benzyl ester hydrochloride (259 mg, 1.12 mmol, Sigma), and triethylamine (0.31 mL, 2.22 mmol, Aldrich) were added. The mixture was stirred for 5 min. and then DCC (233 mg, 1.13 mmol, Aldrich) was added, rinsing the sides of the flask with 0.5 mL of THF. The mixture was allowed to slowly warm to room temperature.

After 18 h, the mixture was cooled in an ice bath and ethyl acetate (4.3 mL) was added. The resulting mixture was filtered, evaporated and purified by flash column chromatography on silica gel (100% ethyl acetate) which gave slightly impure product (475 mg). Recrystallization (hexanes/ethyl acetate) gave the pure amide of Example 17 (176 mg, 0.34 mmol, 34%).

EXAMPLE 18

(S)-2-{(1R,2S,3R,4R)-3-[5-2-(2-methoxycarbonyl-ethyl)-benzyl]-7-oxa-bicyclo[2.2.1]hept-2-yl}-4,5-dihydro-oxazole-4-carboxylic acid benzyl ester. PPh$_3$ (120 mg, 0.46 mmol, Aldrich) and i-Pr$_2$NEt (82 µL, 0.47 mmol, Aldrich) were added to a solution of the amide of Example 17 (153 mg, 0.30 mmol) in dry CH$_2$Cl$_2$ (0.26 mL, Aldrich) and dry CH$_3$CN (1.0 mL, Aldrich). CCl$_4$ (43 µL, 0.45 mmol, Aldrich) was added dropwise and after 4 h of stirring, the solution was cooled in an ice bath and ethyl acetate (3 mL) and saturated aqueous NaHCO$_3$ solution (1 mL) were added. The mixture was poured into saturated aqueous NaCl solution (10 mL) and was extracted with ethyl acetate (10 mL). The organic portion was washed with saturated aqueous NaCl solution (10 mL) and then was dried (MgSO$_4$), filtered, evaporated and purified by flash column chromatography on silica gel (2:1 EtOAc/hexanes) to give the oxazoline of Example 18 (102 mg, 0.21 mmol, 69%).

EXAMPLE 19

2-{(1R,2S,3R,4R)-3-[5-fluoro-2-(2-methoxycarbonyl-ethyl)-benzyl]-7-oxa-bi cyclo[2.2.1]hept-2-yl}-oxazole-4carboxylic acid benzyl ester. The oxazoline of Example 18 was co-evaporated with benzene and then taken into dry CH$_2$Cl$_2$ (1 mL, Aldrich). The solution was cooled in an ice bath and DBU (30 µL, 0.20 mmol, Aldrich) and BrCCl$_3$ (19 µL, 0.19 mmol, Aldrich) were added. The solution was allowed to stand at 0° C. for 17 h and then was diluted with CH$_2$Cl$_2$ (10 mL). The CH$_2$Cl$_2$ solution was washed with saturated aqueous NH$_4$Cl solution (2×5 mL) and the combined aqueous solution extracted with EtOAc (2×10 mL). The combined organic solution was dried (MgSO$_4$), filtered, evaporated, and purified by flash column chromatography on silica gel (40% ethyl acetate/hexanes) to give the oxazole of Example 19 (74 mg, 0.15 mmol, 75%).

EXAMPLE 20

2-{(1R,2S,3R,4R)-3-[5-fluoro-2-(2-methoxycarbonyl-ethyl)-benzyl]-7-oxa-bi cyclo[2.2.1]hept -2-yl}-oxazole-4-carboxylic acid. Pd(OH)$_2$/C (17 mg, 20%, Aldrich) was added to a solution of the oxazole of Example 19 (74 mg, 0.15 mmol) in ethyl acetate (1.4 mL, B & J brand). The mixture was stirred under a balloon of H$_{2(g)}$ for 2 h and then was filtered through celite. Evaporation of the ethyl acetate left the acid of Example 20 (63 mg, 0.16 mmol, 100%) as a white crystalline solid.

EXAMPLE 21

3-(2-{(1R,2R,3S,4R)-3-[4-(4-Cyclohexyl-butylcarbamoyl)-oxazol-2-yl ]-7-oxa-bicyclo[2.21]hept-2-ylmethyl)-4-fluoro-phenyl)-propionic acid methyl ester. The acid of Example 20 (26 mg, 0.064 mmol) was co-evaporated with benzene and the residue taken into dry CH$_2$Cl$_2$ (0.3 mL, Aldrich). Dry DMF (small drop, Aldrich) was added followed by (COCl)$_2$ (11 µL, 0.13 mmol, Aldrich) which caused immediate gas evolution. After 30 min., the volatiles were removed and the residue co-evaporated twice with toluene to leave an off-white solid.

The crude acid chloride was taken into dry CH$_2$Cl$_2$ (0.36 mL, Aldrich) and Et$_3$N (21 µL, 0.15 mmol, Aldrich) was added. 4-cyclohexylbutylammonium chloride (18 mg, 0.094 mmol) was then added and the reaction stirred for 1.5 h. The mixture was partitioned between 10 mL EtOAc and 10 mL 1 M HCl. The aqueous layer was extracted with 10 mL EtOAc and the combined EtOAc solution dried (MgSO$_4$), filtered, evaporated, and purified by flash column chromatography on silica gel (50% EtOAc/hexanes) to give the ester of Example 21 (27 mg, 0.05 mmol, 78%) as a white solid.

EXAMPLE 22

3-(2-{(1R,2R,3S,4R)-3-[4-(4-Cyclohexyl-butylcarbamoyl)-oxazol-2-yl ]-7-oxa-bicyclo[2.2.1]hept-2-ylmethyl}-4-fluoro-phenyl)-propionic acid. A solution of the ester of Example 21 (26 mg, 0.048 mmol) in THF (0.15 mL, Aldrich) and MeOH (0.75 mL, B&J Brand) was treated with 1 M NaOH solution (0.29 mL, 0.29 mmol). After 17 h, The solution was partitioned between 10 mL CH$_2$Cl$_2$ and 10 mL 1 M HCl. The aqueous layer was extracted with CH$_2$Cl$_2$ (2×10 mL) and the combined CH$_2$Cl$_2$ solution dried (MgSO$_4$), filtered, evaporated, and purified by flash column chromatography on silica gel (5% MeOH/CH$_2$Cl$_2$) to give the oxazole of Example 22 (24 mg, 0.046 mmol, 95%) as a white solid.

500 MHz $^1$H NMR (CDCl$_3$, ppm) δ 8.13 (s, 1 H) 7.11–7.08 (m, 2 H) 6.85–6.80 (m, 2 H) 4.97 (d, J=4.4 Hz, 1 H) 4.37 (d, J=4.8 Hz, 1 H) 3.4–3.3 (m, 3 H) 2.84 (t, J=7.7 Hz, 2 H) 2.6–2.5 (overlapping m, 3 H) 2.35 (dd, J=14.5, 11.2 Hz, 1 H) 2.20 (dd, J=14.5, 4.9 Hz, 1 H) 1.9–1.1 (overlapping m, 20 H) 0.9–0.8 (m, 2 H).

MS (EI) m/z 526.2831 (526.2843 calculated for C$_{30}$H$_{39}$FN$_2$O$_5$; error=2 ppm).

EXAMPLE 23

Figure 4:
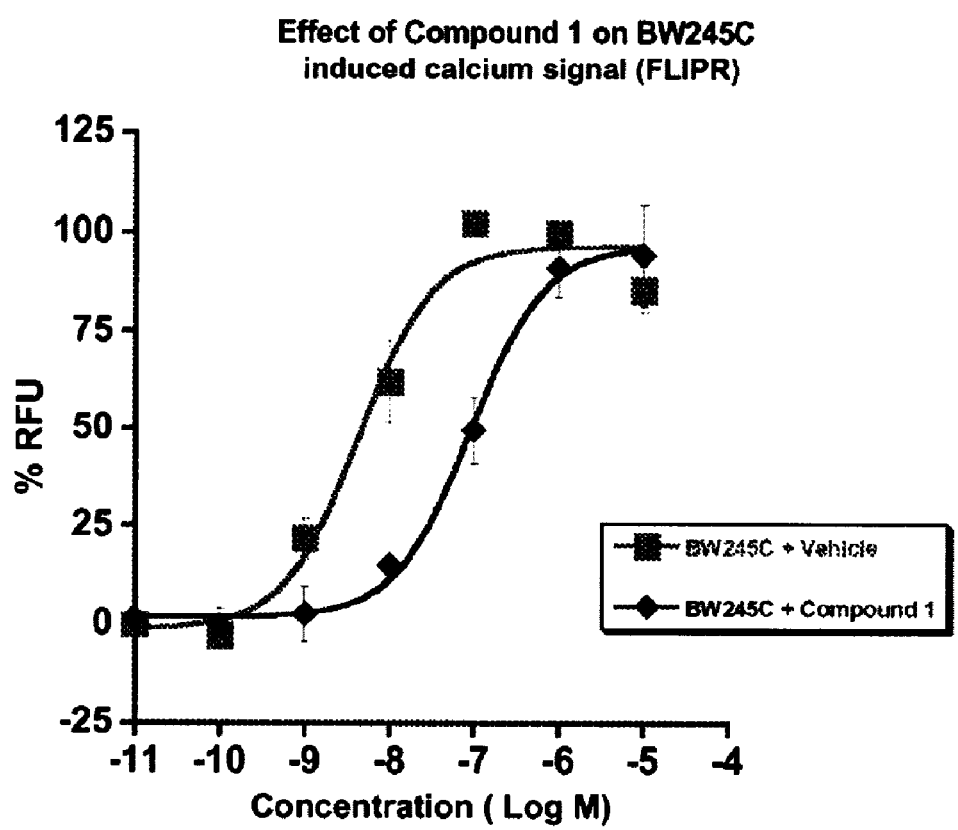
FIG. 4 shows the effect of compound 1 on the activity of BW245C, a known prostaglandin DP agonist, on the induced calcium signal in HEK-293(EBNA) cells stably transfected with human DP-receptor and Gqs5 cDNA (FLIPR).

Determination of the effect of compound 1 on the activity of BW245C on the induced calcium signal (FIG. 4): HEK-293(EBNA) cells, stably expressing cDNAs for the human DP receptor and Gqs5 proteins, were seeded at a density of 5×10$^4$ cells per well in Biocoat® Poly-D-lysine-coated black-wall, clear-bottom 96-well plates (Becton-Dickinson) and allowed to attach overnight in an incubator at 37° C.

Cells were then washed twice with HBSS-HEPES buffer (Hanks Balanced Salt Solution without bicarbonate and phenol red, 20 mM HEPES, pH 7.4) using a Denley Cell-wash plate washer (Labsystems; Franklin, Mass.). After 45–60 min of dye-loading in the dark using the calcium-sensitive dye Fluo-4 AM, at a final concentration of 2 μM, plates were washed four times with HBSS-HEPES buffer to remove excess dye and leaving 100 μl buffer in each well. Plates were then placed into a FLIPR™ instrument and were allowed to equilibrate at 37° C. Drug solution was added in a 50 μl volume to each well to give the desired final concentration. Cells were excited with an Argon laser at 488 nm, and emission was measured through a 510–570 nm bandwidth emission filter (FLIPR™, Molecular Devices, Sunnyvale, Calif.). The peak increase in fluorescence intensity was recorded for each well. On each plate, the standard agonist BW245C was tested over a $10^{-11}$ to $10^{-5}$ molar concentration range in the presence of vehicle or test drug. Concentration-effect curves for BW245C, as depicted in FIG. 1, in the presence of vehicle and test drug were generated. FIG. 1 demonstrates the antagonistic activity of compound 1 at the human DP receptor indicated by a dextral shift of the concentration-effect curve of BW245C in the presence of compound 1 (at $10^{-6}$ molar concentration) relative to vehicle control.

EXAMPLE 24

A nasal spray comprising compound 1 is administered to a patient 5 times per day until the symptoms subside.

EXAMPLE 25

An eye drop comprising compound 1 is administered 4 times per day to a patient suffering from tearing and itching as a result of an allergic response. The patient experiences relief of symptoms as long as the drops are administered throughout the allergy season.

EXAMPLE 26

An aerosol formulation comprising compound 1 is inhaled 2 to 3 times per day by a patient suffering from asthma. Relief of symptoms is experienced for as long as the treatment is continued.

EXAMPLE 27

Compound 1 is administered orally once per day as a sustained-release tablet to a female patient suffering from irritable bowel syndrome. Substantial relief from the symptoms is experienced for as long as the therapy continues.

The present invention is not to be limited in scope by the exemplified embodiments, which are intended as illustrations of individual aspects of the invention. Indeed, various modifications of the invention in addition to those shown and described herein will become apparent to those skilled in the art from the foregoing description. Such modifications are intended to fall within the scope of appended claims.

What is claimed is:

1. A pharmaceutical product comprising

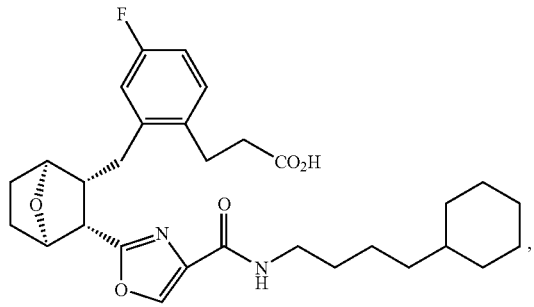

or a pharmaceutically acceptable salt or prodrug thereof, and a pharmaceutically acceptable excipient; wherein said product is packaged and labeled for the treatment of a disease or condition selected from the group consisting of allergic conditions, pain, pulmonary congestion, pulmonary hypotension, sleep disorders and sleep-wake cycle disorders.

2. A compound of the formula

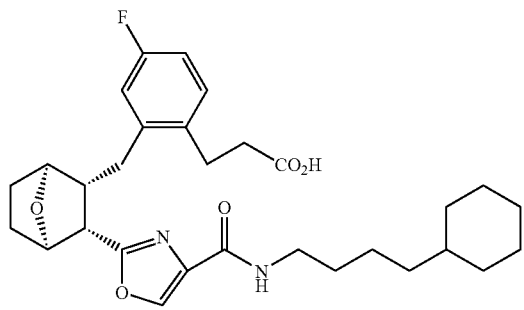

or a pharmaceutically acceptable salt or a prodrug thereof.

3. A pharmaceutical composition comprising

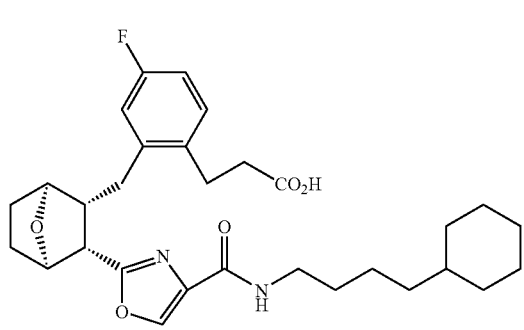

or a pharmaceutically acceptable salt or a prodrug thereof, and a pharmaceutically acceptable excipient.

* * * * *

UNITED STATES PATENT AND TRADEMARK OFFICE
CERTIFICATE OF CORRECTION

PATENT NO. : 7,217,725 B2
APPLICATION NO. : 10/780441
DATED : May 15, 2007
INVENTOR(S) : Krauss et al.

It is certified that error appears in the above-identified patent and that said Letters Patent is hereby corrected as shown below:

On The Title Page, Item -54-, in "Title", line 1, delete "D2" and insert -- $D_2$ --, therefor.

On The Title Page, Item -56-, under "Foreign Patent Documents", line 1, delete "837 0582" and insert -- 837 052 --, therefor.

On The Title Page, Item -56-, under "Foreign Patent Documents", line 3, delete "9/1999" and insert -- 12/1999 --, therefor.

On The Title Page, Item -56-, under "Other Publications", line 10, delete "otent" and insert -- potent --, therefor.

On The Title Page, Item -56-, under "Other Publications", line 11, delete "D2" and insert -- $D_2$ --, therefor.

On The Title Page, Item -56-, under "Other Publications", line 17, delete "D2" and insert -- $D_2$ --, therefor.

On The Title Page, Item -56-, under "Other Publications", line 19, delete "Rockfeller" and insert -- Rockefeller --, therefor.

On The Title Page, Item -56-, under "Other Publications", line 24, delete "D2" and insert -- $D_2$ --, therefor.

On The Title Page, Item -56- pg. 2, under "Other Publications", line 7, delete "D2" and insert -- $D_2$ --, therefor.

On The Title Page, Item -56- pg. 2, under "Other Publications", line 3, delete "D2" and insert -- $D_2$ --, therefor.

On The Title Page, Item -56- pg. 2, under "Other Publications", line 5, delete "D2" and insert -- $D_2$ --, therefor.

In column 1, line 1, delete "D2" and insert -- $D_2$ --, therefor.

In column 1, line 48, delete "D2" and insert -- $D_2$ --, therefor.

In column 1, line 50, delete "D2" and insert -- $D_2$ --, therefor.

In column 1, line 57, after "1993)" insert -- . --.

In column 2, line 2, after "115)" insert -- . --.

UNITED STATES PATENT AND TRADEMARK OFFICE
CERTIFICATE OF CORRECTION

PATENT NO.       : 7,217,725 B2
APPLICATION NO.  : 10/780441
DATED            : May 15, 2007
INVENTOR(S)      : Krauss et al.

It is certified that error appears in the above-identified patent and that said Letters Patent is hereby corrected as shown below:

In column 2, line 7, delete "D2" and insert -- $D_2$ --, therefor.

In column 3, line 55, delete "Prostadglandin" and insert -- Prostaglandin --, therefor.

In column 4, line 3, delete "gastrointesintal" and insert -- gastrointestinal --, therefor.

In column 9, line 9, before "3aR" insert -- [ --.

In column 9, line 15, delete "quenced" and insert -- quenched --, therefor.

In column 9, line 21, delete "4R-3" and insert -- 4R)-3 --, therefor.

In column 9, line 22, delete "[2.21]" and insert -- [2.2.1] --, therefor.

In column 9, line 23, delete "(3aR" and insert -- [3aR --, therefor.

In column 9, line 43, delete "salary oxy[" and insert -- silanyloxy] --, therefor.

In column 9, line 44, delete "ylmethl" and insert -- ylmethyl --, therefor.

In column 9, line 59, delete "silanyl oxy)" and insert -- silanyloxy] --, therefor.

In column 9, line 61, delete "]2.2.1]hept -2ylmethyl" and insert -- [2.2.1]hept-2-ylmethyl --, therefor.

In column 10, line 49, delete "7oxa" and insert -- 7-oxa --, therefor.

In column 10, line 56, delete "bicyclo [2.2.1]" and insert -- bicyclo[2.2.1] --, therefor.

In column 11, line 3, delete "4R)- 3-5" and insert -- 4R)-3-[5 --, therefor.

In column 11, line 4, delete "benzyl ]" and insert -- benzyl] --, therefor.

In column 11, line 28, delete "bicyc lo" and insert -- bicyclo --, therefor.

In column 11, line 49, delete "oxa-bi cyclo" and insert -- oxa-bicyclo --, therefor.

In column 11, line 50, delete "4carboxylic" and insert -- 4-carboxylic --, therefor.

In column 11, line 67, delete "oxa-bi cyclo" and insert -- oxa-bicyclo --, therefor.

UNITED STATES PATENT AND TRADEMARK OFFICE
CERTIFICATE OF CORRECTION

PATENT NO. : 7,217,725 B2
APPLICATION NO. : 10/780441
DATED : May 15, 2007
INVENTOR(S) : Krauss et al.

It is certified that error appears in the above-identified patent and that said Letters Patent is hereby corrected as shown below:

In column 11, line 67, delete "hept -2" and insert -- hept-2 --, therefor.

In column 12, line 13, delete "yl ]" and insert -- yl] --, therefor.

In column 12, line 13, delete "[2.21]" and insert -- [2.2.1] --, therefor.

In column 12, line 13, delete "ylmethyl)" and insert -- ylmethyl} --, therefor.

In column 12, line 37, delete "yl ]" and insert -- yl] --, therefor.

In column 12, line 41, delete "The" and insert -- the --, therefor.

Signed and Sealed this

Seventh Day of August, 2007

JON W. DUDAS
*Director of the United States Patent and Trademark Office*